United States Patent [19]

Teng

[11] Patent Number: 4,510,135
[45] Date of Patent: Apr. 9, 1985

[54] ORALLY ADMINISTERED HEPARIN

[75] Inventor: Lin-nar L. Teng, Bothell, Wash.

[73] Assignee: Research Corporation, New York, N.Y.

[21] Appl. No.: 370,155

[22] Filed: Apr. 21, 1982

[51] Int. Cl.³ .................. A61K 31/73; A61K 31/725; C08B 37/10
[52] U.S. Cl. ........................................ 514/56; 536/21; 514/822
[58] Field of Search ............................ 536/21; 424/183

[56] References Cited

U.S. PATENT DOCUMENTS

| | | | |
|---|---|---|---|
| 2,989,438 | 6/1961 | Nomine et al. | 536/21 |
| 3,058,884 | 10/1962 | Mozen et al. | 536/21 |
| 3,160,563 | 12/1964 | Nazzareno | 536/21 |
| 3,232,837 | 2/1966 | Nomine et al. | 536/21 |
| 3,337,409 | 8/1967 | Williams | 536/21 |
| 4,302,368 | 11/1981 | Dudley et al. | 524/546 |

Primary Examiner—Sam Rosen
Attorney, Agent, or Firm—Scully, Scott, Murphy & Presser

[57] ABSTRACT

An orally administrable heparin comprising: a complex of heparin with (1) a protonated tertiary organic ammonium ion having the formula:

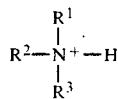

wherein $R^1$, $R^2$ and $R^3$ each independently represent a branched or unbranched alkyl group of 1 to 12 carbon atoms, which may be unsubstituted or substituted with hydroxy or alkoxy groups, or $R^1$ and $R^3$ together with the N atom can form a pyrrolidine, imidazole or morpholine ring; or (2) an ester-containing quaternary ammonium ion having the formula:

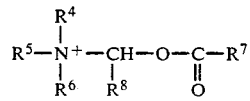

wherein
$R^4$, $R^5$ and $R^6$ each independently represent a branched or unbranched alkyl group of 1 to 12 carbon atoms, which may be unsubstituted or substituted with hydroxy or alkoxy groups, or $R^4$ and $R^6$ together with the N atom can form a pyrrolidine, imidazole or morpholine ring;
$R^7$ represents an alkyl group of 4 to 16 carbon atoms; and
$R^8$ represents a hydrogen atom or a methyl group.

19 Claims, No Drawings

ORALLY ADMINISTERED HEPARIN

BACKGROUND OF THE INVENTION

1. Field of the Invention

This invention relates to the provision of heparin in an orally administrable form.

2. Description of the Prior Art

It has long been established that heparin is an effective and safe blood anticoagulant. However, therapeutic use of heparin is limited by the need to administer it parenterally. A great deal of effort has been spent on the development of adjuvants, derivatives, analogs and expedients to render heparin absorbable from the intestine, so that it may be orally administered. This effort includes adjuvants such as heparin co-administered with ethylenediaminetetraacetate, EDTA (Windsor et al, "Gastrointestinal Absorption of Heparin and Synthetic Heparinoids", Nature, 190, 263–264 (1961); Tidball et al, "Enhancement of Jejunal Absorption of Heparinoid by Sodium Ethylenediaminetetraacetate in the Dog", Proc. Soc. Exp. Biol. Med., 111, 713–715 (1962); Rebar et al, "Forderung der Gastrointestinalen Resorption von Heparin durch Calciumbindungsmittel", Experientia, 19, 141–142 (1963)), with dimethylsulfoxide, DMSO, and diethylsulfone, and their homologs (Koh, T. Y., "Intestinal Absorption of Heparin", Can. J. Biochem., 47, 951–954 (1969)); derivatives such as heparin that underwent partial desulfation and methylation (Salafsky et al, "Intestinal Absorption of a Modified Heparin", Proc. Soc. Exp. Biol. Med., 104, 62–65 (1960)) or heparinic acid and/or heparinic acid complexes (Koh et al, "Intestinal Absorption of Stable Heparin Acid Complexes," J. Lab. Clin. Med., 80(1), 47–55 (1972)); analogs (Jarrett et al, "Effect of Intravenous and Oral Admnistration of Heparinoids G 31150, G-31150-A, and of Nitrolotriacetic Acid on Blood Coagulation", Throm. Diath Haemorrh, 25, 187–200(1971)); and expedients, such as instillation of heparin in acidic solutions in the animal intestinal loop (Loomis, T. A., "Absorption of Heparin from the Intestine", Proc. Soc. Exp. Med., 101, 447–449 (1959); Sue, T. K., "Heparin, Physical and Biological Factors in Absorption" in "Heparin: Structure, Cellular Functions and Clinical Applications", Ed., N. M. McDuffie, Academic Press, New York, 1979, pp. 159–166). Windsor, U.S. Pat. No. 3,088,868, discloses orally administrable heparin comprising heparin complexed with the alkali metal salts of amino acids or polyaminepolyacids, e.g., salts of EDTA. Koh et al, U.S. Pat. Nos. 3,506,642 and 3,577,534, disclose heparin complexed with weakly basic compounds (pKB=7.0–12.5) being useful as an orally active medicament. However, too highly basic materials, e.g., aliphatic amines, are taught to produce materials which are not orally active. Engel et al, U.S. Pat. No. 3,574,832, discloses a heparin composition for oral, intraduodenal or rectal administration comprising heparin and a sulfate-tupe surfactant. Sache et al, U.S. Pat. No. 4,239,754, discloses orally active heparin compositions comprising heparin retained on or in liposomes, the lipids of said liposomes are preferably phospholipids comprising acyl chains derived from nonsaturated fatty acids.

While limited success has been achieved in the direction of increasing heparin absorbability from the intestine, these efforts have not yet reached the stage that heparin can be administered orally to give a sustaining systemic anticoagulant effect. In short, these efforts to develop an orally administered heparin for use in clinical anticoagulant therapy have so far been unsuccessful.

In related work, complexes of heparin with quaternary ammonium ions such as tridodecylmethyl ammonium chloride, TDMAC (Leininger et al, Science, 152, 1625(1966); Grode et al, J. Biomed. Mater. Res. Symp., 3,77 (1972)), benzalkonium chloride, BKC (Grode et al, J. Biomed. Mater. Res. Symp., 3,77 (1972); Gott, U. L., Adv. Exp. Med. Bio., 52 35 (1975)), and cetylpyridinium chloride, GPC (Schmer et al, Trans. Am. Soc. Artif. Intern. Organs, 22,654 (1976)), have been proven to render heparin soluble in organic solvents. The heparin-surfactant complexes have been successful in the coating of internal surfaces of plastic medical appliances. Chang, U.S. Pat. No. 3,522,346, discloses the preparation of non-thrombogenic microcapsules wherein the encapsulating membrane incorporates or has on its surface a quaternary ammonium-heparin complex. Suitable quaternary ammonium compounds are benzalkonium, cetyltrimethylammonium and cetyldimethylbenzyl-ammonium. Harumiya et al, U.S. Pat. No. 3,844,989, discloses antithrombogenic polymer compositions, useful in the production of medical appliances, comprising a polymer containing cationic monomer units and heparin internally bound thereto. Grotta, U.S. Pat. No. 3,846,353, discloses a method of making a non-thrombogenic plastic material by exposing the plastic to a water-insoluble, organic solvent-soluble long chain alkyl quaternary ammonium salt having 2–4 alkyl groups and then exposing the plastic to heparin. Subsequent exposure of the plastic to blood plasma failed to release heparin in an anticoagulant effective amount. Ericksson et al, U.S. Pat. No. 4,265,927, discloses a method of heparinizing the surface of a medical article by contacting the article with a complex of heparin and a cationic surfactant, preferably of the primary amine type. Marchisio et al, U.S. Pat. No. 3,865,723, discloses the use of polymers with a polyamidic-aminic structure to remove heparin from blood.

Surfactants like BKC and CPC are cationic surfactants and widely used as antimicrobials (The Extra Pharmacocopia, Matindale, 27th Ed., The Pharmaceutical Press, London (1977)) and are quite toxic, e.g., $LD_{50}$ of CPC, i.v. (mouse) is 10 mg/kg, i.v. (rat) is 6 mg/kg (Registry of Toxic Effects of Chemical Substances, U.S. Dept. HEW, 1975 Edition). Their toxicity is related to those various biological effects of quaternary ammonium heads whose effects include the depolarization of muscle tissue and hemolysis of erythrocytes. Toxic symptoms include dyspnoea and cyanosis due to paralysis of the respiratory muscles, possibly leading to asphyxia (Gastmeier et al, Z. Ges. Gerich. Med., 65, 96 (1969)) and allergic reactions, after repetitive applications of quaternary ammonium salt solutions to the skin, which have been reported to occur in some patients (Morgan, J. K., Br. J. Clin. Prac. 22, 261 (1969); Lansdown et al, Br. J. Derm., 86, 361(1972)). It is also believed that the surfactant characteristics of the quaternary ammonium ion, particularly in the liver, causes additional alterations in a number of chemical, biological and transport phenomena (Bohr et al, "Labile Quaternary Ammonium Salt as Soft Antimicrobials", J. Med Chem. 23, 469–474 (1980)).

A need therefore continues to exist for an orally administrable heparin.

SUMMARY OF THE INVENTION

Accordingly, one object of the invention is to provide an orally administrable heparin.

Another object of the invention is to provide an orally administrable heparin which is free of toxic side-effects or degradation products.

A further object of the invention is to provide a heparin complex which renders heparin hydrophobic and lipophilic.

Briefly, these objects and other objects of the invention as hereinafter will become more readily apparent can be attained by providing a complex of heparin with a protonated tertiary organic ammonium ion having the formula:

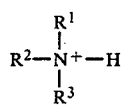

wherein $R^1$, $R^2$ and $R^3$ each independently represent a branched or unbranched alkyl group of 1 to 12 carbon atoms, which may be unsubstituted or substituted with hydroxy or alkoxy groups, or $R^1$ and $R^3$ together with the N atom can form a heterocyclic ring of the formula:

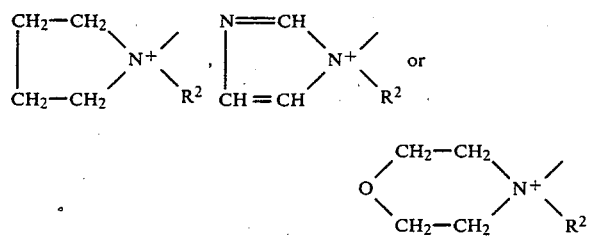

wherein $R_2$ has the meaning set forth above or an ester-containing quaternary ammonium ion having the formula

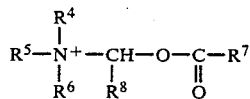

wherein $R^4$ $R^5$ and $R^6$ each independently represent a branched or unbranched alkyl group of 1 to 12 carbon atoms, which may be unsubstituted or substituted with hydroxy or alkoxy groups, or $R^4$ and $R^6$ together with the N atom can form a heterocyclic ring of the formula:

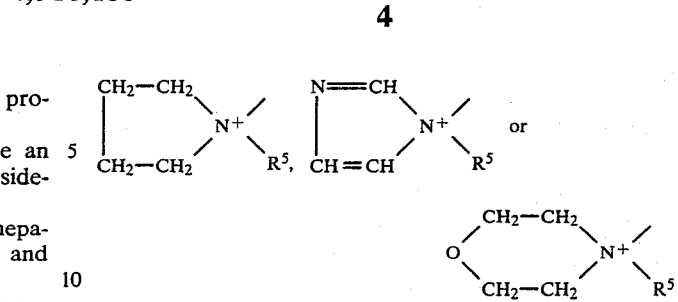

wherein
  $R^5$ has the meaning set forth above
  $R^7$ represents an alkyl group of 4 to 16 carbon atoms; and
  $R^8$ represents a hydrogen atom or a methyl group.

DETAILED DESCRIPTION OF THE PREFERRED EMBODIMENTS

It has now been discovered that heparin forms complexes with certain "soft" or "pseudo" quaternary ammonium ions to render heparin hydrophobic and lipophilic to thereby carry heparin through the lipid barrier of the intestinal wall and, consequently, increase the absorbability of heparin from the intestine. A systemic anticoagulant effect can thereby be achieved.

It will be understood that heparin is a very complex molecule, and a structure which has not been completely elucidated. It is tentatively identified as a sulfated copolymer consisting of alternating 1–4 α linked glucosamine and glucuronic acid residues. In accordance with the invention, heparin is combined with certain quaternary ammonium ions, which in themselves are not simple. Therefore the specific structure of the resulting product cannot be stated with certainty and the terminology "complex" is used to embrace the structures which may be formed. Preferably, the complex contains five moles of the ammonium ion of this invention per mole of heparin tetrasaccharide unit, it being believed that complexation occurs with the sulfate groups of the tetrasaccharide unit. For purposes of illustration a schematic representation of the repeating heparin tetrasaccharide unit (sodium salt) is shown below

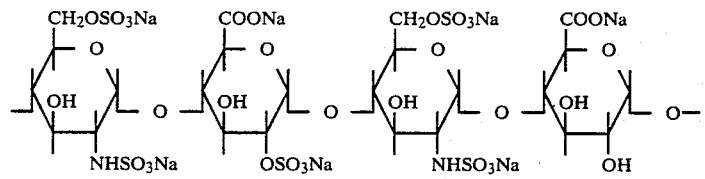

Specifically complexes of heparin with (1) trialkyl ammonium ion, formula I,

(I)

wherein $R^1$, $R^2$ and $R^3$ each independently represent a branched or unbranched alkyl group of 1 to 12 carbon atoms, the alkyl groups being optionally substituted with hydroxy groups or alkoxy groups such as methoxy or ethoxy, e.g., $HN^+(CH_3)(CH_2CH_2OCH_2CH_3)_2$, or $R^1$ and $R^3$ together with the N atm can form a heterocyclic (pyrolidine, imidazole or morpholine) ring of the formula:

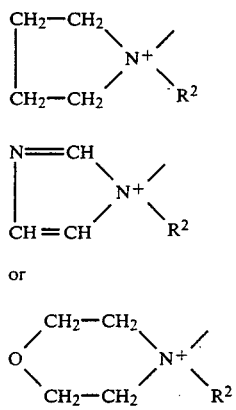

wherein in formulae Ia, Ib and Ic, $R^2$ has the meaning as set forth above, preferably methyl or with (2) an alkanoyloxy-alkyl trialkyl ammonium ion, formula II:

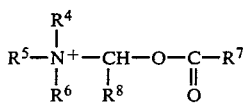

wherein $R^4$, $R^5$ and $R^6$ each independently represent a branched or unbranched alkyl group of 1 to 12 carbon atoms, preferably, 1 to 5 carbon atoms, the alkyl groups being optionally substituted with hydroxy groups or alkoxy groups such as methoxy or ethoxy, or $R^4$ and $R^6$ together with the N atom can form a heterocyclic (pyrrolidine, imidazole or morpholine) ring of the formula:

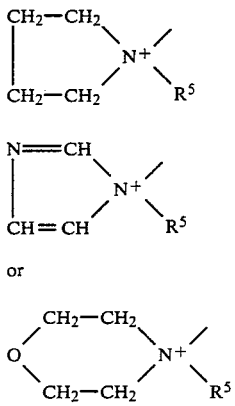

wherein in formulae IIa, IIb and IIc, $R^5$ has the meaning as set forth above, preferably, methyl;

$R^7$ represents an alkyl group of 4 to 16 carbon atoms, preferably, 7 to 15 carbon atoms, and $R^8$ represents a hydrogen atoms or a methyl group; represent the novel complexes of the present invention.

The quaternary ammonium ions can be readily prepared by methods known in the art. The quaternary ammonium ion of formula (I) can be prepared by bringing the corresponding amine into contact with a mineral acid, e.g., HCl, or a carboxylic acid, e.g., acetic acid:

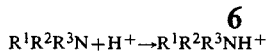

wherein $R^1$, $R^2$ and $R^3$ are as defined above.

The quaternary ammonium ion of formula (II) can be prepared in two steps, (i) preparation of the corresponding α-chloro alkyl ester and (ii) formation of the desired quaternary ammonium ion:

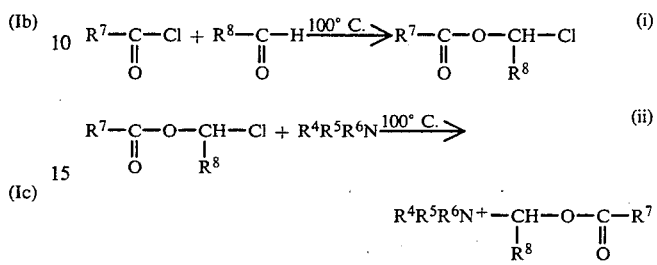

wherein $R^4$, $R^5$, $R^6$, $R^7$ and $R^8$ are as defined above.

In reaction (i), above, typically, equimolar amounts of aldehyde and acyl chloride are mixed and heated between 90° and 100° C. for three to six hours. This heating can be done in the presence of a solvent, e.g., purified petroleum ether (B.Pt. 94°–105° C.), or without a solvent. The reaction mixture is refluxed in a dry atmosphere. The α-chloro alkyl ester can then be recovered in purified form by column chromatography, e.g., on Florisil using petroleum ether (B.Pt. 30°–60° C.), or via recrystallization from petroleum either (B.Pt. 30°–60° C.).

In reaction (ii), above, the α-chloro alkyl ester is mixed with the desired tertiary amine in equimolar ratio and is heated or allowed to react for an appropriate period of time, e.g., from 3 to 48 hours. The desired quaternary ammonium salt separates as a solid by triturating the reaction mixture with anhydrous ether. The solid is isolated by filtration under a nitrogen atmosphere, is thoroughly washed with anhydrous ether, and dried in vacuo over calcium sulfate at room temperature.

The heparin complexes of the present invention are formed by bringing heparin into contact with the desired quaternary ammonium ion. For example, an aqueous solution of heparin sodium salt is mixed with the quaternary ammonium salt, preferably the chloride of formula I or II to give heparin-quaternary ammonium ion complexes and sodium chloride. Consequently, heparin in the heparin complex is a mucopolysaccharide chain with negative sulfate groups on it associated with the positive quaternary ammonium groups, but still with sodium associated with the carboxylic acid groups. As noted above, the reaction may be conveniently performed in aqueous media. The reaction conditions are quite simple, i.e. mixing aqueous solutions of the appropriate quantity of heparin sodium salt and the quaternary ammonium salt at room temperature, preferably five moles of quaternary ammonium salt are used per mole of heparin tetrasaccharide unit. The product may be readily recovered by lyophilization, since sodium chloride, the other product resulting from the above reaction, possesses no adverse effect when it is co-administered orally with the heparin complex. Alternatively, the heparin-quaternary ammonium ion complex may be separated from sodium chloride by gel filtration chromatography with water as the elution solvent. Lyophilization of the elution pool that contains the complex gives the desired purified product.

The heparin complexes of the present invention can be orally administered, per se, for example, as a lyophilized powder, or in combination with a pharmaceutically acceptable excipient, e.g., with water as a dispersion or in the form of a tablet, and exhibit a sustained systemic anticoagulant effect. Exemplary excipients include inert fillers and binders such as lactose, sucrose, dextrose, sorbitol and cellulose products; disintegrating agents such as starch and soy polysaccharide; and lubricants such as magnesium stearate, stearic acid and hydrogenated vegetable oils.

Additionally, encapsulation of the complex in an enteric coating, by means well-known in the art, provides a suitable form for oral administration.

The heparin complexes of the present invention may also be administered in the form of a vaginal or rectal suppository, cream or ointment. The formulation of such suppositories, creams and ointments can be acomplished by techniques well known in the art.

While the quaternary ammonium ions of formulae (I) and (II) may both be used in the above-noted formulations, formula (I) is preferably used in preparing orally administrable formulations, and, formula (II) is preferably used in preparing formulations for vaginal or rectal administration.

Typically, the heparin complexes of this invention are used in amount to provide a dosage of 1400 units of heparin per kg of body weight every 8 to 12 hours. This dosage being sufficient to exhibit a saturated systemic anticoagulant activity.

It has also been found that when the heparin complexes of the present invention are prepared with a stoichiometric excess of quaternary ammonium ion being present in the final product, the ease of absorption of heparin through the intestine is increased. Typically, the heparin complex will contain between five moles of quaternary ammonium ion per mole of heparin tetrasaccharide unit and three parts by weight of quaternary ammonium ion per one part by weight of heparin.

Unlike the surfactants of the prior art, the above-noted formulations are "soft" or "pseudo" quaternary ammonium ions. That is, they will be deprotonated in vivo as in the formula I ions, and/or hydrolyzed in vivo to give protonated triethyl amine, a fatty acid and an aldehyde molecule as in the formula II ions. Consequently, they are non-toxic and eminently suited for oral administration.

Having generally described this invention, a further understanding can be obtained by reference to certain specific examples which are provided herein for purposes of illustration only and are not intended to be limiting unless otherwise specified.

Specifically, complexes of heparin with triethyl ammonium ion

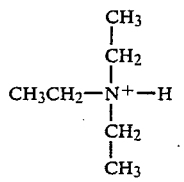

and that with 1-(n-dodecanoyloxy)-ethyl triethyl ammonium ion

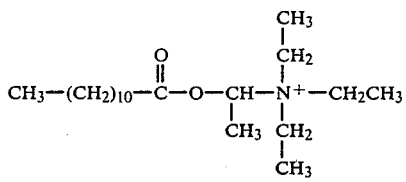

in a ratio of one mole of tetrasaccharide unit of heparin to five moles of the ammonium ion have been administered through the esophagus of non-fasting rats.

EXAMPLE 1

The results of oral administration of triethyl ammonium • heparin complex of two different dosages into rats of two different age groups as compared with those of oral or intravenous (i.v.) admnistration of commercial heparin alone are summarized in Table 1.

TABLE 1

| Anticoagulent Activity (Unit/ml, determined by APTT) In Rat Plasma After Heparin Administration | | | | | | | | |
|---|---|---|---|---|---|---|---|---|
| Route of Administration (Form of Drug) | Body Weight (# rat) | Heparin Dosage μ/kg | Time After Heparin Administration (min) | | | | | |
| | | | 0 | 15 | 30 | 45 | 60 | 90 |
| Oral (Heparin.Et$_3$NH complex) | 415.5 ± 43.9 (5) | 3839 ± 450 (24.61 ± 2.89) mg/kg | 0 | 1.55 ± 2.26 | .38 ± .26 | .42 ± .49 | .53 ± .74 | .56 ± .52 |
| Oral (Heparin.Et$_3$NH Complex) | 609 ± 8.8 (4) | 2839 ± 190 (18.80 ± 1.22) mg/kg | 0 | .10 ± .07 | .16 ± .13 | .18 ± .10 | .11 ± .08 | .12 ± .05 |
| Oral (Heparin alone) | 415.5 ± 47.1 (6) | 3992 ± 373 (25.59 ± 2.39) mg/kg | 0 | .03 ± .04 | .03 ± .05 | .05 ± .06 | .03 ± .05 | .03 ± .06 |
| I.V. (Heparin alone) | 375.1 ± 4.5 (6) | 164.5 ± 9.2 (1.05 ± .06) mg/kg | 0 | 1.72 ± .62 | 1.02 ± .45 | .82 ± .73 | .52 ± .51 | .29 ± .44 |
| Oral (Heparin.Et$_3$NH— 1:3 By Wt.) | 526 ± 41 (6) | 1825 ± 282 (11.72 ± 1.81) mg/kg | 0 | .17 ± .29 | .13 ± .10 | .12 ± .10 | .19 ± .08 | .60 ± 1.15 |
| Duodenum (Heparin.Et$_3$NH— 1:3 By Wt.) | 561 ± 52 (6) | 1535 ± 320 (9.84 ± 2.05) mg/kg | 0 | .06 ± .07 | .11 ± .16 | .14 ± .20 | .13 ± .08 | .07 ± .09 |
| Route of Administration (Form of Drug) | Body Weight (# rat) | Heparin Dosage μ/kg | Time After Heparin Administration (min) | | | | | |
| | | | 120 | 180 | 240 | 300 | 360 | 420 480 |
| Oral Heparin.Et$_3$NH | 415.5 ± 43.9 (5) | 3839 ± 450 (24.61 ± 2.89) | .41 ± .41 | .28 ± .36 | .35 ± .33 | .41 ± .40 | .45 ± .37 | |

TABLE 1-continued

Anticoagulent Activity (Unit/ml, determined by APTT) In Rat Plasma After Heparin Administration

| complex) | | mg/kg | | | | | | | |
|---|---|---|---|---|---|---|---|---|---|
| Oral (Heparin.Et₃NH Complex) | 609 ± 8.8 (4) | 2839 ± 190 (18.80 ± 1.22) mg/kg | .11 ± .09 | .12 ± .06 | .16 ± .12 | .16 ± .16 | .17 ± .07 | .14 ± .11 | .09 ± .01 |
| Oral (Heparin alone) | 415.5 ± 47.1 (6) | 3992 ± 373 (25.59 ± 2.39) mg/kg | .03 ± .04 | .02 ± .04 | 0 | .03 ± .04 | 0 | 0 | |
| I.V. (Heparin alone) | 375.1 ± 4.5 (6) | 164.5 ± 9.2 (1.05 ± .06) mg/kg | .20 ± .22 | .33 ± .41 | .04 ± .09 | | | | |
| Oral (Heparin.Et₃NH— 1:3 By Wt.) | 526 ± 41 (6) | 1825 ± 282 (11.72 ± 1.8) mg/kg | .09 ± .10 | .12 ± .12 | .11 ± .07 | .07 ± .08 | .10 ± .09 | .25 ± .08 | .20 ± .01 |
| Duodenum (Heparin.Et₃NH— 1:3 By Wt.) | 561 ± 52 (6) | 1535 ± 320 (9.84 ± 2.05) mg/kg | .06 ± .08 | .13 ± .11 | .18 ± .05 | .18 ± .20 | .92 ± 1.65 | .31 ± .30 | .03 ± .05 |

With younger rats and higher dosage (24.61 mg/kg), a strong systemic anticoagulant effect was produced which lasted for 5 hours. With older rats and lower dosage (18.80 mg/kg), a steady, appreciable systemic anticoagulant effect was produced for 8 hours. Conversely, in control studies, almost no systemic anticoagulant effect was produced by the oral administration of commercial heparin alone. Compared with intravenous administration of commercial heparin, oral administration of heparin complex is about 1/20 to 1/25 as effective as intravenous commercial heparin, but, the anticoagulant effect of the complex lasted longer. By variation of the side chains of the quaternary ammonium ion, e.g., lengthening, branching, and substitution with OH or alkoxy, the systemic anticoagulant effect may be appreciably enhanced.

The effect of the presence of excessive triethyl ammonium ion on the absorbability of heparin from the intestine was also investigated. The mixture of heparin and triethyl ammonium ion in a ratio of heparin:triethyl ammonium chloride=1:3 by weight was administered orally through the esophagus or duodenally through the duodenum of the rat. These results are also summarized in Table 1.

As shown, heparin is more easily absorbed from the intestine when it is in the presence of excessive ammonium ion. With about ⅔ of the dosage of heparin that was given to the older rats, the plasma anticoagulant activities of the rats subjected to oral administration (11.72 mg/kg) and those subjected to duodenal administration (9.84 mg.kg) give compatible profiles. Further, the peaks of plasma anticoagulant activity are present as two waves in the time-course studies. In oral adminstration, a stronger peak appears around 90 min. after administration and a weaker peak, around 240 min. after administration. In the duodenal administration, a weak peak appears at 45 min. and a stronger one around 360 min. after administration.

The APTT (activated partial thromboplastin time) test used to evaluate the anticoagulant activity herein determines the time for recalcified plasma to clot after incubation with a reagent (AUTOMATED APTT-available from General Diagnostics, Division of Warner-Lambert Company, Morris Plains, N.J.) comprising a platelet phospholipid and a contact activator (micronized silica) which is a measure of the rate at which thrombin is formed via the intrinsic pathway of coagulation.

The experimental animals were non-fasting and allowed to eat and drink during the experiments. As a result, the peaks of plasma anticoagulant activities varied greatly with each individual animal. The large standard deviations of plasma anticoagulant activity at each time interval are a result of this protocol.

The fact that the systemic anticoagulant effect observed in the oral administration of the heparin complex is due to the presence of heparin in circulating blood, is further supported by the following observation. Heparin was isolated and identified by microelectrophoresis from the pool of plasma samples (about 1.0 ml of what was left from APTT assays) of one older rat subjected to oral administration of heparin complex at the lower dosage (i.e. 18 mg/kg). Conversely, no heparin was either isolated or observed by microelectrophoresis from the plasma sample pool (also about 1.0 ml) of a rat subjected to oral administration of commercial heparin alone at the dosage of 25 kg/mg.

EXAMPLE 2

A lyophilized complex of heparin with 1-(n-dodecanoyloxy)-ethyl triethyl ammonium ion was orally administered to four rats. Among them, two showed slight or no anticoagulant activity for three hours. The other two, however, showed appreciable and sustained systemic anticoagulant activity 15 minutes after administration, and the effect lasted for six hours. The results are summarized in Table 2. The esterate moiety of this quaternary ammonium salt may not always survive in the acidic environment of the stomach.

TABLE 2

Anticoagulant Activities (unit/ml, Determined by APTT) In Rat Plasma After Oral Administration of Heparin ol-(n-Dodecanoyloxy)-Ethyl Triethyl Ammonium Complex

| | | Dosage | | Time After Heparin Administration (min) | | | | | | | | | |
|---|---|---|---|---|---|---|---|---|---|---|---|---|---|
| # Rat | Bd. Wt. | Heparin mg/kg | Complex mg/kg | 0 | 15 | 30 | 60 | 90 | 120 | 180 | 240 | 300 | 360 |
| 164 | 485/5 | 13.89 | 22.90 | 0 | 0 | 0 | 0 | 0 | 0 | 0 | | | |
| 165 | 406.3 | 15.38 | 25.36 | 0 | .19 | .13 | .14 | .18 | .13 | .23 | .11 | .19 | .15 |
| 167 | 475.2 | 12.16 | 21.04 | 0 | 0 | 0 | 0 | 0 | 0 | 0 | | | |

TABLE 2-continued

Anticoagulant Activities (unit/ml, Determined by APTT) In Rat Plasma After Oral Administration of Heparin ol-(n-Dodecanoyloxy)-Ethyl Triethyl Ammonium Complex

| | | Dosage | | Time After Heparin Administration (min) | | | | | | | | | |
|---|---|---|---|---|---|---|---|---|---|---|---|---|---|
| # Rat | Bd. Wt. | Heparin mg/kg | Complex mg/kg | 0 | 15 | 30 | 60 | 90 | 120 | 180 | 240 | 300 | 360 |
| 168 | 460.2 | 16.08 | 26.50 | 0 | .18 | .11 | .15 | .23 | .44 | .70 | .18 | 1.12 | .63 |

Whether heparin will remain intact depends on the relative rate of its deactivation in the low pH environment of the stomach versus the rate of its complex formation with the triethyl ammonium ion generated in situ (i.e. the 1-(n-dodecanoyloxy)-ethyl triethyl ammonium ion hydrolyzes to give a molecule of n-dodecanoic acid, a molecule of acetaldehyde, and a molecule of protonated triethyl amine (triethyl ammonium ion)). However, the added lipophilicity due to the esterate moiety enables this quaternary ammonium ion to be an ideal carrier ion for heparin in rectal or vaginal application.

Having now fully described this invention, it will be apparent to one of ordinary skill in the art that many changes and modifications can be made thereto without departing from the spirit or scope of the invention set forth herein.

What is claimed as new and intended to be covered by Letters Patent is:

1. A complex of heparin with a protonated tertiary organic ammonium ion, wherein said ammonium ion has the formula:

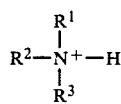

wherein $R^1$, $R^2$ and $R^3$ each independently represent a branched or unbranched alkyl group of 1 to 12 carbon atoms, which may be unsubstituted or substituted with hydroxy or alkoxy groups, or $R^1$ and $R^3$ together with the N atom can form a heterocyclic ring of the formula:

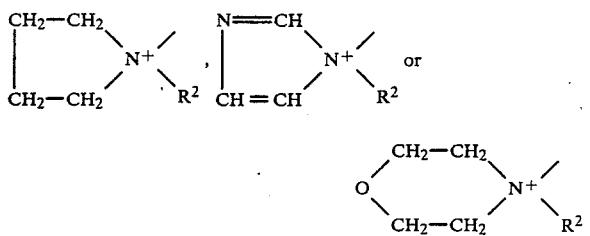

wherein $R^2$ has the meaning set forth above.

2. The complex according to claim 1, wherein $R^1$, $R^2$ and $R^3$ each independently represent a branched or unbranched alkyl group of 1 to 12 carbon atoms, which may be unsubstituted or substituted with hydroxy or alkoxy groups.

3. The complex according to claim 1 or 2, wherein said ammonium ion is present in a ratio of 5 moles of ammonium ion to 1 mole of heparin tetrasaccharide unit.

4. The complex according to claim 1 or 2, wherein said ammonium ion is present in a stoichiometric excess over the amount necessary to form a complex with heparin.

5. A complex of heparin with an ester-containing quaternary ammonium ion, wherein said ammonium ion has the formula:

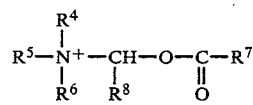

wherein $R^4$, $R^5$ and $R^6$ each independently represent a branched or unbranched alkyl group of 1 to 12 carbon atoms, which may be unsubstituted or substituted with hydroxy or alkoxy groups, or $R^4$ and $R^6$ together with the N atoms can form a heterocyclic ring of the formula:

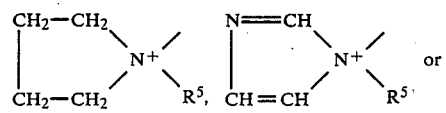

wherein $R^5$ has the meaning set forth above;

$R^7$ represents an alkyl group of 4 to 16 carbon atoms; and $R^8$ represents a hydrogen atom or a methyl group.

6. The complex according to claim 5, wherein $R^4$, $R^5$ and $R^6$ each independently represent a branched or unbranched alkyl group of 1 to 12 carbon atoms, which may be unsubstituted or substituted with hydroxy or alkoxy groups.

7. The complex according to claim 6, wherein said alkyl group is of 1 to 5 carbon atoms.

8. The complex according to claim 5 or 6, wherein said ammonium ion is present in a ratio of 5 moles of ammonium ion to 1 mole of heparin tetrasaccharide unit.

9. The complex according to claim 5 or 6, wherein said ammonium ion is present in a stoichiometric excess over the amount necessary to form a complex with heparin.

10. A blood anticoagulant composition comprising an anticoagulant effective amount of the complex according to claim 1 and a pharmaceutically acceptable excipient.

11. The composition according to claim 10, in the form of a tablet.

12. The composition according to claim 10, in the form of an aqueous dispersion.

13. A blood anticoagulant composition comprising an anticoagulant effective amount of the complex according to claim 5 and a pharmaceutically acceptable excipient.

14. The composition according to claim 13, in the form of a cream.

15. The composition according to claim 13, in the form of an ointment.

16. The composition according to claim 13, in the form of a suppository.

17. The process of orally administering a blood anticoagulant to a mammal which comprises orally administering in a blood anticoagulant effective amount a complex of heparin with a protonated tertiary organic ammonium ion, wherein said ammonium ion has the formula:

$$R^2-\overset{R^1}{\underset{R^3}{N^+}}-H$$

wherein $R^1$, $R^2$ and $R^3$ each independently represent a branched or unbranched alkyl group of 1 to 12 carbon atoms, which may be unsubstituted or substituted with hydroxy or alkoxy groups, or $R^1$ and $R^3$ together with the N atom can form a heterocyclic ring of the formula:

$$\begin{array}{c}CH_2-CH_2\\ |\qquad\qquad N^+\\ CH_2-CH_2\end{array}\diagdown R^2 \quad , \quad \begin{array}{c}N=CH\\ |\qquad\qquad N^+\\ CH=CH\end{array}\diagdown R^2$$

$$O\diagup\begin{array}{c}CH_2-CH_2\\ \diagdown N^+\\ CH_2-CH_2\end{array}\diagdown R^2$$

wherein $R^2$ has the meaning set forth above.

18. The process of orally administering a blood anticoagulant to a mammal which comprises orally administering in a blood anticoagulant effective amount a complex of heparin with an ester-containing quaternary ammonium ion, wherein said ammonium ion has the formula:

$$R^5-\overset{R^4}{\underset{R^6}{N^+}}-\overset{}{\underset{R^8}{CH}}-O-\overset{}{\underset{O}{C}}-R^7$$

wherein $R^4$, $R^5$ and $R^6$ each independently represent a branched or unbranched alkyl group of 1 to 12 carbon atoms, which may be unsubstituted or substituted with hydroxy or alkoxy groups, or $R^4$ and $R^6$ together with the N atom can form a heterocyclic ring of the formula:

$$\begin{array}{c}CH_2-CH_2\\ |\qquad\qquad N^+\\ CH_2-CH_2\end{array}\diagdown R^5 \quad , \quad \begin{array}{c}N=CH\\ |\qquad\qquad N^+\\ CH=CH\end{array}\diagdown R^5 \quad \text{or}$$

$$O\diagup\begin{array}{c}CH_2-CH_2\\ \diagdown N^+\\ CH_2-CH_2\end{array}\diagdown R^5$$

wherein
$R^5$ has the meaning set forth above;
$R^7$ represents an alkyl group of 4 to 16 carbon atoms; and
$R^8$ represents a hydrogen atom or a methyl group.

19. A complex of heparin with a protonated tertiary organic ammonium ion, wherein said ammonium ion has the formula:

$$R^2-\overset{R^1}{\underset{R^3}{N^+}}-H$$

wherein $R^1$, $R^2$ and $R^3$ each independently represents a branched or unbranched alkyl group of 1 to 5 carbon atoms, which may be unsubstituted or substituted with hydroxy or alkoxy groups, or $R^1$ and $R^3$ together with the N atom can form a heterocyclic ring of the formula:

$$\begin{array}{c}CH_2-CH_2\\ |\qquad\qquad N^+\\ CH_2-CH_2\end{array}\diagdown R^2 \quad , \quad \begin{array}{c}N=CH\\ |\qquad\qquad N^+\\ CH=CH\end{array}\diagdown R^2 \quad \text{or}$$

$$O\diagup\begin{array}{c}CH_2-CH_2\\ \diagdown N^+\\ CH_2-CH_2\end{array}\diagdown R^2$$

wherein $R^2$ has the meaning set forth above.

* * * * *

UNITED STATES PATENT AND TRADEMARK OFFICE
CERTIFICATE OF CORRECTION

PATENT NO. : 4,510,135
DATED : April 9, 1985
INVENTOR(S) : Lin-nar L. Teng

It is certified that error appears in the above-identified patent and that said Letters Patent is hereby corrected as shown below:

On the Title Page, before Section [54] insert the following: --"This invention was made with government support under grant number R01 HL 22035 awarded by the National Institutes of Health. The government has certain rights in the invention."--

Signed and Sealed this

Fifth Day of October, 1993

Attest:

BRUCE LEHMAN

*Attesting Officer*     *Commissioner of Patents and Trademarks*